United States Patent
Ackermann et al.

(10) Patent No.: US 11,922,668 B2
(45) Date of Patent: Mar. 5, 2024

(54) ASYNCHRONOUS REGION-OF-INTEREST ADJUDICATION FOR MEDICAL IMAGES

(71) Applicant: Google LLC, Mountain View, CA (US)

(72) Inventors: Rebecca Ackermann, Mountain View, CA (US); William Chen, Mountain View, CA (US); Thad Hughes, Mountain View, CA (US); Teagan Daly, Mountain View, CA (US); Scott McKinney, Mountain View, CA (US); Rory Sayres, Mountain View, CA (US); Quang Duong, Mountain View, CA (US); Jacob Stimes, Mountain View, CA (US); Eric Lindley, Mountain View, CA (US); Cristhian Cruz, Mountain View, CA (US); Beverly Freeman, Mountain View, CA (US)

(73) Assignee: Google LLC, Mountain View, CA (US)

( * ) Notice: Subject to any disclaimer, the term of this patent is extended or adjusted under 35 U.S.C. 154(b) by 210 days.

(21) Appl. No.: 17/520,538

(22) Filed: Nov. 5, 2021

(65) Prior Publication Data
US 2022/0138482 A1    May 5, 2022

Related U.S. Application Data

(60) Provisional application No. 63/110,137, filed on Nov. 5, 2020.

(51) Int. Cl.
*G06V 10/22* (2022.01)
*G06F 3/04815* (2022.01)
(Continued)

(52) U.S. Cl.
CPC ........ *G06V 10/235* (2022.01); *G06F 3/04815* (2013.01); *G06F 3/0484* (2013.01); *G16H 30/40* (2018.01)

(58) Field of Classification Search
CPC .. G06V 10/235; G16H 30/40; G06F 3/04815; G06F 3/0484
See application file for complete search history.

(56) References Cited

U.S. PATENT DOCUMENTS 10,013,781 B1   7/2018  Gammage et al.
11,003,948 B1 *  5/2021  Douglas .............. G16H 30/40
(Continued)

OTHER PUBLICATIONS

Schaekermann et al., Remote Tool-Based Adjudication for Grading Diabetic Retinopathy, Translational Vision Science and Technology vol. 8 No. 6 (Dec. 2019).

(Continued)

*Primary Examiner* — Daniel Samwel
(74) *Attorney, Agent, or Firm* — McDonnell Boehnen Hulbert & Berghoff LLP

(57) ABSTRACT

A set of user interface tools is described facilitating asynchronous adjudication of one or more regions-of-interest in a medical image by a group of two or more graders, each of which has access to the set of tools in a workstation environment. The set of tools include (1) a feature for enabling the graders to assess the medical image and manually delineate one or more specific regions-of-interest (ROI) in the medical image, (2) a feature for assessing the ROI(s) delineated by other graders, including display of the ROI delineated by other graders; (3) dialog features for explaining and discussing the assessments, including a text feature for discussing the assessments. The dialog features and the ROIs delineated by all the graders are visible to all the graders on the workstation display as they collectively adjudicate the medical image in a round-robin manner. The set of tools further include (4) a feature for manually verifying grader agreement with the other graders' assessments.

20 Claims, 10 Drawing Sheets

(51) Int. Cl.
G06F 3/0484 (2022.01)
G16H 30/40 (2018.01)

(56) References Cited

U.S. PATENT DOCUMENTS

| | | | | |
|---|---|---|---|---|
| 2009/0265229 A1* | 10/2009 | Sidhu | ................... | G06Q 30/02 705/26.1 |
| 2010/0111391 A1* | 5/2010 | Valadez | ................ | G06F 18/254 382/160 |
| 2011/0126127 A1* | 5/2011 | Mariotti | .............. | H04M 7/0027 715/753 |
| 2012/0166546 A1* | 6/2012 | Venon | ................... | G16H 80/00 709/205 |
| 2014/0072192 A1* | 3/2014 | Reiner | ................... | G16H 40/20 382/128 |
| 2014/0229881 A1* | 8/2014 | Schadewaldt | ....... | G06F 3/04855 715/771 |
| 2015/0149565 A1* | 5/2015 | Ahmed | ................ | H04L 65/401 709/204 |
| 2020/0043614 A1* | 2/2020 | Washida | ............. | H04L 12/1822 |
| 2020/0185113 A1* | 6/2020 | Nicolson | ................ | G16H 30/40 |

OTHER PUBLICATIONS

Murphy, "PACS: Invaluable and Inevitable", Ophthalmology Management Article, Jun. 1, 2013.
Holz et al., "Agreement among ophthalmologists in evaluating fluorescein angiograms in patients with neovascular age-related macular degeneration for photodynamic therapy eligibility (FLAP-study)".
Wong et al., "Interobserver Variability in Structure Delineation of Organs at Risk on Cone Beam CT using Raystation TPS v4.5.2", Journal of Medical Imaging and Radiation Sciences Research Informing Practice, vol. 48, Issue 1, Supplement, S4-S5, Mar. 1, 2017.
Saba et al., "Inter-observer Variability Analysis of Automatic Lung Delineation in Normal and Disease Patients", 40(6), Jun. 2016.
Joskowicz et al., "Inter-observer variability of manual contour delineation of structures in CT", European Radiology, 29, pp. 1391-1399, 2019.
Lee et al., "Ocular neovascularization: an epidemiologic review", Surv Ophthalmol, Nov.-Dec. 1998, 43(3):245-69.
Fleming et al., "Automated grading for diabetic retinopathy: a large-scale audit using arbitration by clinical experts", Br J Ophthalmol, Dec. 2010, 94(12), pp. 1606-1610.
Elmore et al., "Variability in Radiologists' Interpretations of Mammograms", The New England Journal of Medicine, vol. 331, No. 22, Dec. 1, 1994.
Uji et al., "Variability of Retinal Thickness Measurements in Tilted or Stretched Optical Coherence Tomography Images", translational vision science & technology, vol. 6, No. 2, Article 1, 2017.
Krause et al., "Grader variability and the importance of reference standards for evaluating machine learning moels for diabetic retinopathy", Jul. 3, 2018.
Ryan et al., "Development and Evaluation of Reference Standards for Image-based Telemedicine Diagnosis and Clinical Research Studies in Ophthalmology", pp. 1902-1910.
Guan et al., "Who Said What: Modeling Individual Labelers Improves Classification", Jan. 4, 2018, 10 pages.
Campochiaro, "Ocular Neovascularization", J. Mol. Med., Mar. 2013; 91(3); 311-321.
Neely et al., "Ocular Neovascularization" American Journal of Pathology, vol. 153, No. 3, Sep. 1998, pp. 665-670.
Cohen et al., "Types of choroidal neovascularisation in newly diagnosed exudative age-related macular degeneration", Br J. Ophthalmol 2007; 91:1173-1176.

* cited by examiner

UI Tools

FIG. 5

Stack 1 | Stack 2

Look through the other graders' ROIs and or responses below. Do you agree with their assessments? (* Required)
○ No
○ Yes Please identify all suspicious regions Group answers

● G2

ROI 1
Select all reasons that make this region suspicious? — Discoloration
Severity on a scale of 1-10? — 3
Other comments to add? — NA
Patient followup recommendation? — Followup immediately

● G3

ROI 2

ROI 1

Comments — See all

Enter a comment

G3 ROI 1 — 70
G1 ROI 2 — 72
74
56
12A
12B

Image 1/2
Zoom: 89.87%

FIG. 6

Look through the other graders' ROIs and or responses below. Do you agree with their assessments? (* Required)

○ No
○ Yes

Please identify all suspicious regions
Group answers

ROI 1
● G2

| Select all reasons that make this region suspicious? | Discoloration |
| Severity on a scale of 1- 10? | 3 |
| Other comments to add? | NA |
| Patient followup recommendation? | Followup immediately |

ROI 2
● G3

ROI 1
⬈ See all

Comments
Enter a comment

Comment History

Initial submission (G1) disagree. I have a strong rationale for this based on conclusive studies from ADJ 123.

(G2) [ Comment ]

(G3) A comment

Stack 1    Stack 2

G3 ROI 1

ASYNCHRONOUS REGION-OF-INTEREST ADJUDICATION FOR MEDICAL IMAGES

CROSS-REFERENCE TO RELATED APPLICATION

The present application claims priority to Provisional Patent Application No. 63/110,137, filed with the U.S. Patent and Trademark Office on Nov. 5, 2020, the contents of which are hereby incorporated by reference.

BACKGROUND

This disclosure relates to an interface and set of tools enabling a group of human graders to delineate and adjudicate one or more regions-of-interest in a medical image in an asynchronous, round-robin manner. The type of medical image can vary and the set of tools is applicable to a wide variety of types of 2D and 3D medical images, including for example mammography images, CT scans, X-rays, magnified tissue or pathology images, photographic images, e.g., of the skin, fundus images, and the like. The term "medical image" is intended to encompass both still and video images of medical subject matter, for example delineation and adjudication of regions-of-interest in a freeze frame or still image in a video image sequence, e.g., an ultrasound video or a colonoscopy video.

The disclosure has two main applications, one of which is generating region of interest labels for training images used in developing and validating machine-learning models. The methods enable such labels to be obtained accurately and at scale. The other main application is in clinical diagnostics, for example when a medical image is reviewed to obtain a diagnosis that reflects a consensus of multiple experts. In one conceivable implementation one of the "experts" is a machine-learning model.

Standard clinical practice for localization tasks (i.e., identification of particular regions-of-interest in a larger image) is adjudication by clinicians. This is slow, costly, and difficult to scale—and particularly so for assessments that rely on region-of-interest delineation. From physician to physician, regions-of-interest labels can vary greatly in size and placement while still being part of an "accurate" spatial area. The assessment of these labels is therefore subjective, relative, and even pluralistic. Whereas for medical images, text, radio-button or Boolean-based answers to clinical questions can be programmatically determined to be true or false, region-of-interest answers require human assessment due to their unique nature. It will be noted that region-of-interest assessment can be performed using computers, i.e., programmatically, using trained deep learning models, however the present disclosure is directed to tools for facilitating human assessment and adjudication.

The article of Schaekermann et al., *Remote Tool-Based Adjudication for Grading Diabetic Retinopathy*, Translational Vision Science and Technology vol. 8 no. 6 (December 2019), available at https://tvst.arvojournals.org/article.aspx?articleid=2757836, describes a tool for round-robin asynchronous grading of retinal fundus images for diagnosis of diabetic retinopathy. The Schaekermann article does not describe tools for enabling the graders to mark or delineate specific regions-of-interest in the fundus images. Grading is done over the entire image, not specific portions thereof.

SUMMARY

This disclosure features a user interface (UI) with tools for the graders to specifically delineate or draw (using a mouse cursor or a touch screen) specific regions-of-interest, e.g., bounding boxes, circles, lines, points or polygons around specific regions in the medical image, and proceed to comment on and adjudicate these hand-drawn regions-of-interest and not merely the entire image.

In one specific embodiment, a novel suite of tools and user interface is described for remote, asynchronous adjudication of regions-of-interest (ROIs) in medical images. This asynchronous adjudication occurs with a pool of graders in a round-robin fashion. This asynchronous and round-robin approach means that graders can be working on multiple tasks at a time, and individual schedules are not a blocker to getting tasks adjudicated. Another advantage is that the graders can maintain anonymity, which helps avoid bias towards more experienced or socially dominant physicians.

The user interface features including a combination of the following four features:

1. Tools or Features in the UI for Assessing the Original Image and Delineating Specific Regions-of-Interest (ROI).

The interface includes a drawing tool which allows the user to choose the location, size and shape of the ROI and answer any follow-on questions about the marking in a text panel. In one embodiment, each grader's drawing of ROI is in a distinct color to differentiate between graders.

2. Tool or Feature for Assessing Other Graders' ROIs.

Once all graders have made an initial assessment and if there is disagreement, the grader can decide whether to change their answer to align with the assessments of other graders by assessing the other graders' ROIs and answers. In one embodiment the other graders' ROIs appear in contrasting colors (e.g., red and yellow) to help the grader disambiguate their own ROIs. These colors were chosen to be within the same tonal range with the most visual contrast. In the grading and adjudication process, each grader's identity is kept anonymous and non-identifying indicia, such as G1 (Grader 1), G2 (Grader 2), G3 (Grader 3) etc. are applied to each grader's ROIs and comments consistently throughout the rounds of adjudication.

3. Dialog and Text Boxes for Explaining and Discussing the Assessments.

This tool includes a text feature permitting a grader to ask questions about a ROI delineated by other graders and permitting a grader to answer questions about the ROI they delineated wherein the dialog features and the ROIs delineated by all the graders are visible to all the graders on the workstation display as they adjudicate the medical image in a round-robin manner. Graders are identified by their G1, G2, G3 label in the comment history for anonymity and continuity in a back and forth discussion.

4. Tool or Feature for Manually Verifying Grader Agreement.

Because it is difficult to programmatically assess agreement in ROIs with variable margins of error, and because it is actually undesirable to remove expert human visual assessment from the end of the process, each grader must manually attest that the ROIs are in agreement in order for the task to be fully adjudicated. This occurs in a prompt appearing on the UI. This last step ensures that all graders are in agreement and the margin of difference among the ROIs is within the reasonable range for that subspecialty and image type. In case of disagreement, round-robin evaluation proceeds further until unanimity is reached or a limit is reached on the number of rounds of evaluation after which the image is flagged as not having agreement.

In still another aspect, a method of performing an asynchronous adjudication of one or more regions-of-interest in a medical image by a group of two or more graders, each of which has access to the set of tools at a workstation in which the workstation includes a display displaying the medical image. The method includes the steps of (1) providing each of the graders with user interface feature enabling the grader to assess the medical image and manually delineate one or more specific regions-of-interest (ROI) in the medical image on the workstation display;

(2) providing each of the graders with a user interface feature for assessing the ROI delineated by other graders, including display of the ROI delineated by other graders;

(3) providing each of the graders with dialog features for explaining and discussing the assessments, including a text feature permitting a grader to ask questions about a ROI delineated by other graders and permitting a grader to answer questions about the ROI they delineated wherein the dialog features and the ROIs delineated by all the graders are visible to all the graders on their respective workstation display as they adjudicate the medical image in a round-robin, asynchronous manner; and (4) providing each of the graders with a user interface feature for manually verifying grader agreement, wherein if each of the graders verify grader agreement using the feature the adjudication of the medical image is concluded.

In another aspect, we describe a server environment (including a server and associated computer memory, e.g., mass data storage unit) that can be considered a computing platform facilitating asynchronous adjudication of one or more regions-of-interest in a medical image by a group of two or more remotely located graders. The graders communicate with the computing platform over computer networks using workstations. The computing platform includes the computer memory (e.g., mass data storage unit) storing the medical image, and a server distributing the medical image to the workstations used by the two or more graders. The server receives data from the workstations indicating the graders' assessment of the medical image and manually delineation of one or more specific regions-of-interest (ROI) in the medical image as explained previously. The server further receives data from the workstations in the form of text by which the graders assess the ROI delineated by other graders. The server further receives data from the workstations in the form of text explaining and discussing the assessments, optionally including questions about a ROI delineated by other graders and answer to questions about the ROI they delineated, examples of which are shown in the Figures. The server communicates with the workstations such that the text and ROIs delineated by all the graders are visible to all the graders on the workstation display as they adjudicate the medical image in a round-robin manner. The server further receives data indicating manually verifying grader agreement, indicating that the adjudication of the medical image is concluded.

In still another aspect, a method of performing an asynchronous adjudication of one or more regions-of-interest in a medical image by a group of two or more graders is disclosed. Each of the graders has access to the set of tools at a workstation in which the workstation includes a display displaying the medical image. The method includes the steps of (1) receiving and storing in an adjudication computing platform data manually delineating one or more specific regions-of-interest (ROI) in the medical image from the workstations; (2) receiving and storing in the adjudication computing platform data comprising text from the workstations explaining and discussing the assessments, including a text asking questions about a ROI delineated by other graders and answers to questions about the ROI a grader delineated, wherein adjudication computing platform communicates with the workstations such that the text and the ROIs delineated by all the graders are visible to all the graders on their respective workstations as they adjudicate the medical image in a round-robin, asynchronous manner; and (3) receiving and storing data indicating manual agreement from each of the graders on the adjudication of the ROIs.

BRIEF DESCRIPTION OF THE DRAWINGS

FIG. 5 is an illustration of a UI tool in the form of a feature for assessing the ROI(s) delineated by other graders, including display of the ROI(s) delineated by other graders.

FIG. 6 is an illustration of a UI tool in the form of dialog features for explaining and discussing the ROI assessments, including a comment or text feature permitting a grader to ask questions about a ROI delineated by other graders and permitting a grader to answer questions about the ROI they delineated. The dialog features and the ROIs delineated by all the graders are visible to all the graders on the workstation display as they adjudicate the medical image in a round-robin or asynchronous manner.

FIG. 7 is an illustration of a UI feature for manually verifying grader agreement, wherein each of the graders must verify grader agreement using the feature to conclude the adjudication of the medical image.

FIG. 8 is another example of the UI tool allowing the grader to assess the medical image and manually delineate one or more specific regions-of-interest (ROI) in the medical image; in this example they activate the "+draw elliptical ROI" icon on the text panel on the right, they click on the image in "stack 1" and the small crosshair tool appears in stack 1.

FIG. 9 shows the grader having dragged the crosshair tool in stack 1 over to the image and releasing the crosshair tool on the center of the area where the grader wishes to create an ellipse around the ROI. Handles (not shown, but see FIG. 3) on the crosshair tool permit the user to stretch the circle into the shape of an ellipse centered on the ROI.

DETAILED DESCRIPTION

This document describes a set of user interface tools or features that facilitate asynchronous adjudication of one or more regions-of-interest in a medical image by a group of two or more (human) graders, each of which has access to the set of tools in a workstation environment in which each workstation includes a display displaying the medical image. The term "workstation" is intended to be interpreted broadly to encompass any computing device with a display and a user interface for interacting with the display, e.g., using a mouse or a touch sensitive display, such as a desktop computer, tablet computer, smartphone, and the like.

Figure 1:
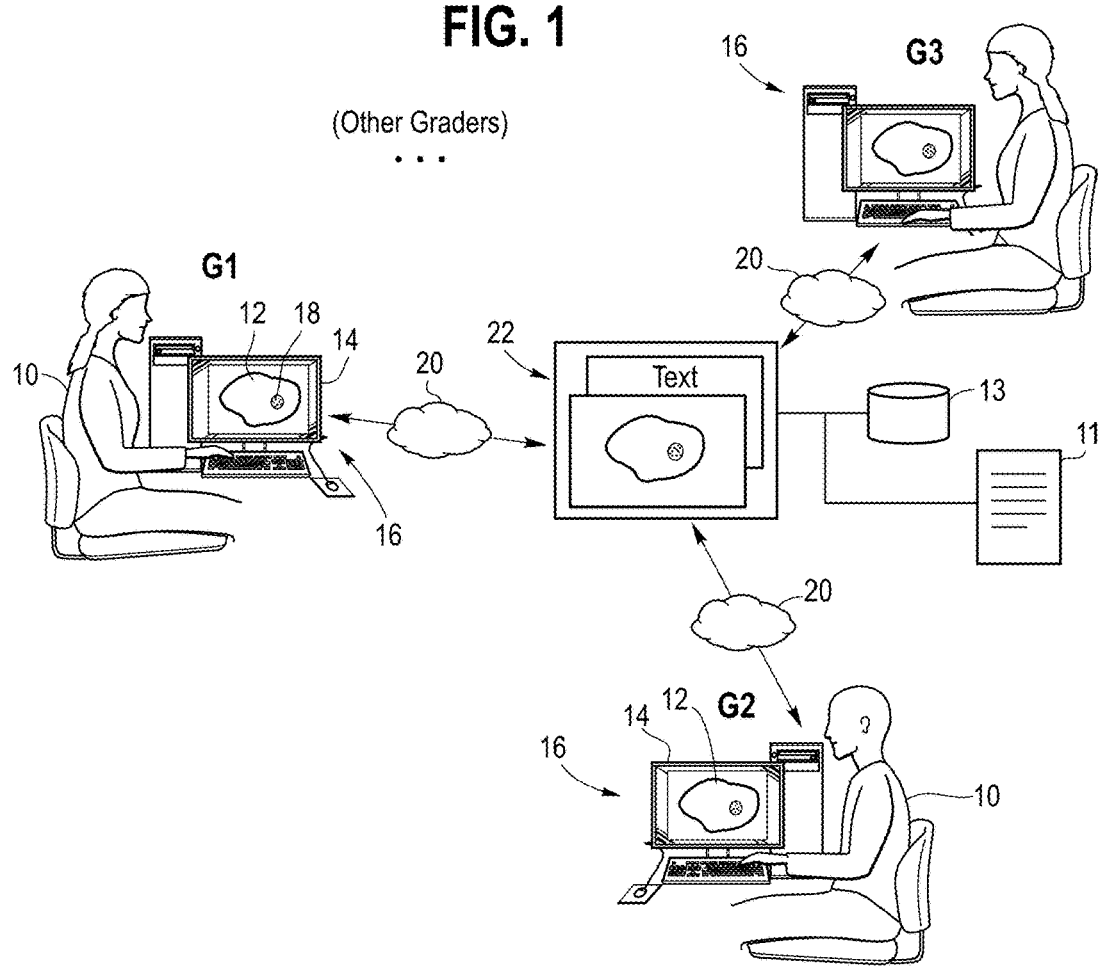
FIG. 1 is an illustration of a set of human graders (G1, G2, etc.) in a workstation environment each viewing a medical image on a display of a workstation. The workstations include a set of user interface tools facilitating asynchronous adjudication of one or more regions-of-interest in a medical image, the set of tools being described in subsequent Figures.

FIG. 1 is an illustration of a set of human graders 10 (G1, G2, etc.) in a workstation environment, each of which are able to view a medical image 12 on a display 14 of a workstation 16. An Image Viewer (software application) is executed in the workstation and configured to display both the medical image 12 and provide for display of the user interface tools and features discussed below. In particular, the workstations 16 include a set of user interface tools facilitating asynchronous adjudication of one or more regions-of-interest in a medical image 12; the set of tools being described in subsequent Figures.

The graders 10 G1, G2, ... typically are not reviewing the medical image 12 at the same time and will view, evaluate, annotate and comment on the image as explained below when their schedule permits, hence the viewing and annotation occur in an asynchronous, round-robin manner and in any conceivable sequence. In other words, and as an example, grader G2 could be the first to view the medical image 12 and delineates their ROI(s) 18 in the image and provides comments, then say three hours later grader G1 views the medical image and delineates their own ROI(s) and comments, including comments or discussion of Grader 2's ROI(s) 18 and G2's comments, after which, say the next day, G3 reviews the medical image 12 and delineates their ROI(s) and adds their comments to those of G1 and G2. G1 and G2 then later on review the comments and ROI(s) of G3 and add their further comments, possibly changing the location and shape of their ROI(s) in response to input from G3, and the process continues in a round-robin, asynchronous fashion until all the graders indicate their agreement with each other's assessments or the process times out or ends indicating disagreement among the graders.

Because any grader could desire to access the medical image 12 with their workstation 16 at any time, the digital file containing the medical image, ROI(s), comments and other text input from the graders is stored in a centralized memory 13; the workstations communicate with a server 11 over computer networks 20, similar to the storage of documents, spreadsheets, and other types of files in a cloud by a service provider such as Google. This central data file containing the image and grader-supplied ROI(s) and text comments is indicated at 22. The server receives the data from the workstations (text, ROI delineations) and updates the central data file and then serves the updated file to the workstations in response to requests from the workstations in an asynchronous manner.

The type of medical image 12 is not particularly important and can vary widely. Examples of the medical image include a CT scan, an X-ray, a mammogram, an MRI, an ultrasound image, a fundus image or set of fundus images, a photograph of an anatomical structure such as skin, and a magnified tissue image. The number of graders is also arbitrary and can vary, from say 2 or 3 to more than that, as may be necessary or desired.

Figure 2:
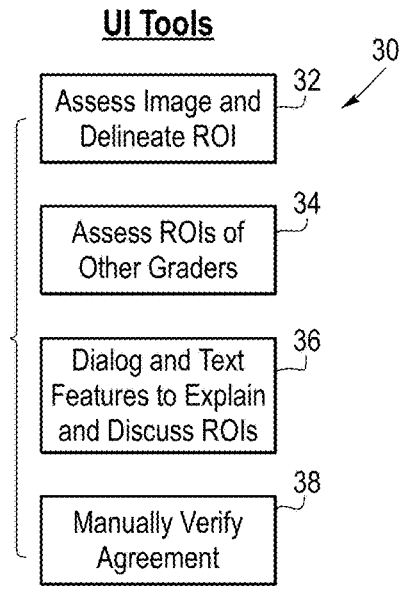
FIG. 2 is an illustration of the UI tools which are provided on each of the workstations of FIG. 1.

FIG. 2 is an illustration of the UI tools 30 which are provided on the display of each of the workstations 16 of FIG. 1. These tools 30 include:

(1) a feature 32 for enabling the graders to assess the medical image and manually delineate one or more specific regions-of-interest (ROI) (18, FIG. 1) in the medical image on the workstation display;

(2) a feature 34 for assessing the ROI delineated by other graders, including display of the ROI delineated by other graders;

(3) dialog features 36 for explaining and discussing the assessments, including a text feature permitting a grader to ask questions about a ROI delineated by other graders and a permitting a grader to answer questions about the ROI they delineated; the dialog features and the ROIs delineated by all the graders are visible to all the graders on the workstation display as they adjudicate the medical image in a round-robin manner; and (4) a feature for manually verifying grader agreement, wherein each of the graders must verify grader agreement using the feature to conclude the adjudication of the medical image. Examples of these tools are shown in the subsequent figures and described below. Variation from the specific of the examples described below is of course possible. The tools can be accessed by various menu options or as icons present on a panel of the Image Viewer, as explained below. Variations from the specifics of the illustrated embodiments will be possible and appreciated by those skilled in the art.

The storage and accessing of the medical images is in a patient de-identified manner in compliance with all state and federal privacy laws (including HIPAA).

Tools (1) A Feature for Enabling the Graders to Assess the Medical Image and Manually Delineate One or More Specific Regions-of-Interest.

Figure 3:
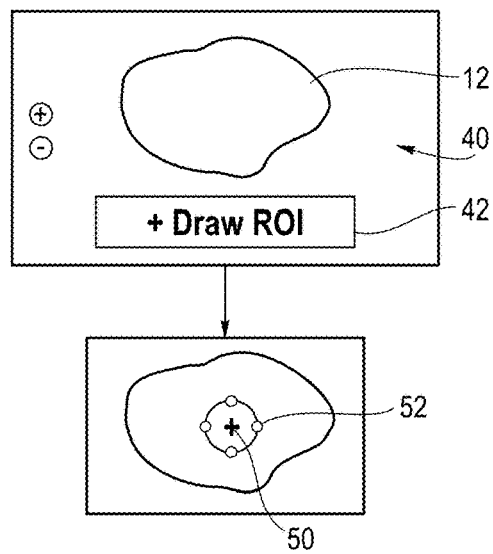
FIG. 3 is an illustration of a UI tool in the form of a feature for enabling the graders to assess the medical image and manually delineate one or more specific regions-of-interest (ROI) in the medical image on the workstation display.

FIG. 3 is an illustration of a UI tool in the form of a feature for enabling the graders to assess the medical image and manually delineate one or more specific ROIs in the medical image on the workstation display. This feature could permit a grader to delineate an ROI in the medical image in the form of a closed curve of any shape (polygon, ellipse, circle, etc.), a point, a line, or a line segment. Typically, a developer or administrator (or the like) of the Image Viewer will ascertain what type of ROI is appropriate for a given type of medical image, and will configure this tool so as to enable a grader to create a ROI of say one or two types, e.g., point and closed polygon curve, or closed polygon curve and ellipse, or point and line segment, just an ellipse, etc. The type of ROI tool the grader may use is determined when the Image Viewer developer configures the task and specifies the ROI shape. The administrator or developer of the Image Viewer may choose elliptical, rectangular, polygonal, line, or point. But once that is determined, the grader may only use the configured tool. This is to ensure that labels created by different graders are consistent and appropriate to the task.

Referring again to FIG. 3, the Image Viewer includes display area 40 where the medical image 12 is shown, and user interface tools to navigate around the image, zoom in and out, etc., e.g., using the actions of a cursor or mouse, and therefore enable the grader to assess the image and determine whether any regions of interest are present. The Image Viewer also includes a button, icon, or other similar feature 42, such a box with text "+Draw ROI", which when activated allows the user to manually delineate a ROI in the displayed medical image 12 using a cursor, mouse, a finger or pen on touch sensitive display, or otherwise. For example, when the user clicks that box 42, the cursor changes to a crosshair 50 to indicate that now the grader may draw an ROI. When the grader clicks over the medical image, a closed curve ROI is created with one corner as the point of click; a "handle" 52 (shown in this example as a small circle within the outline of the ROI) will appear here. The grader can hold and pull the closed curve (e.g., polygon or ellipse) into the desired shape, using the "handles" 52. At any time during the session, the grader may edit the ROI by dragging on one of the handles 52 to change the shape. The ellipse ROI tool only draws ellipses, so it's impossible for the grader to stretch the ROI out of an elliptical shape.

The manner of drawing a closed curve ROI can vary considerably depending on user or system administrator preferences. One possible drawing method that can be used is set forth in the patent to C. Gammage et al., U.S. Pat. No. 10,013,781. The '781 patent is assigned to the assignee of this invention and its entire content is incorporated by reference herein.

Figure 4:
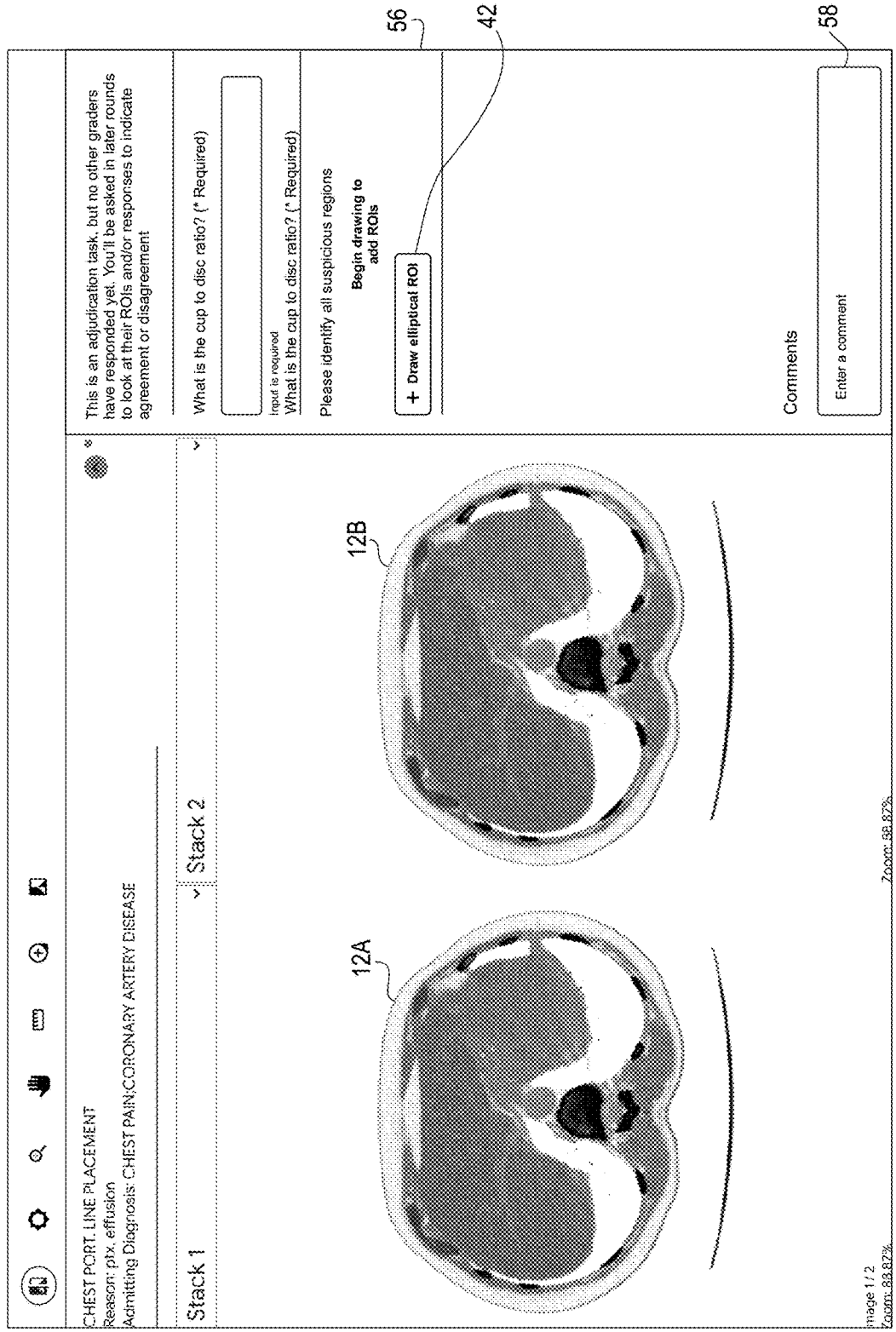
FIG. 4 is another example of the implementation of the first UI tool.

FIG. 4 is another example of the implementation of this first tool. The display includes a display of a medical image 12 and a side panel 56 where the grader is able to add annotations or comments about the image and initiate the delineation of an ROI in the image 12. The grader activates the "+draw elliptical ROI" box and the procedure and tools of FIG. 3 are displayed after the user clicks on a location in the left hand image 12A. The grader can also enter any comments about the ROI they have drawn by typing in the comment box 58.

Figure 8:
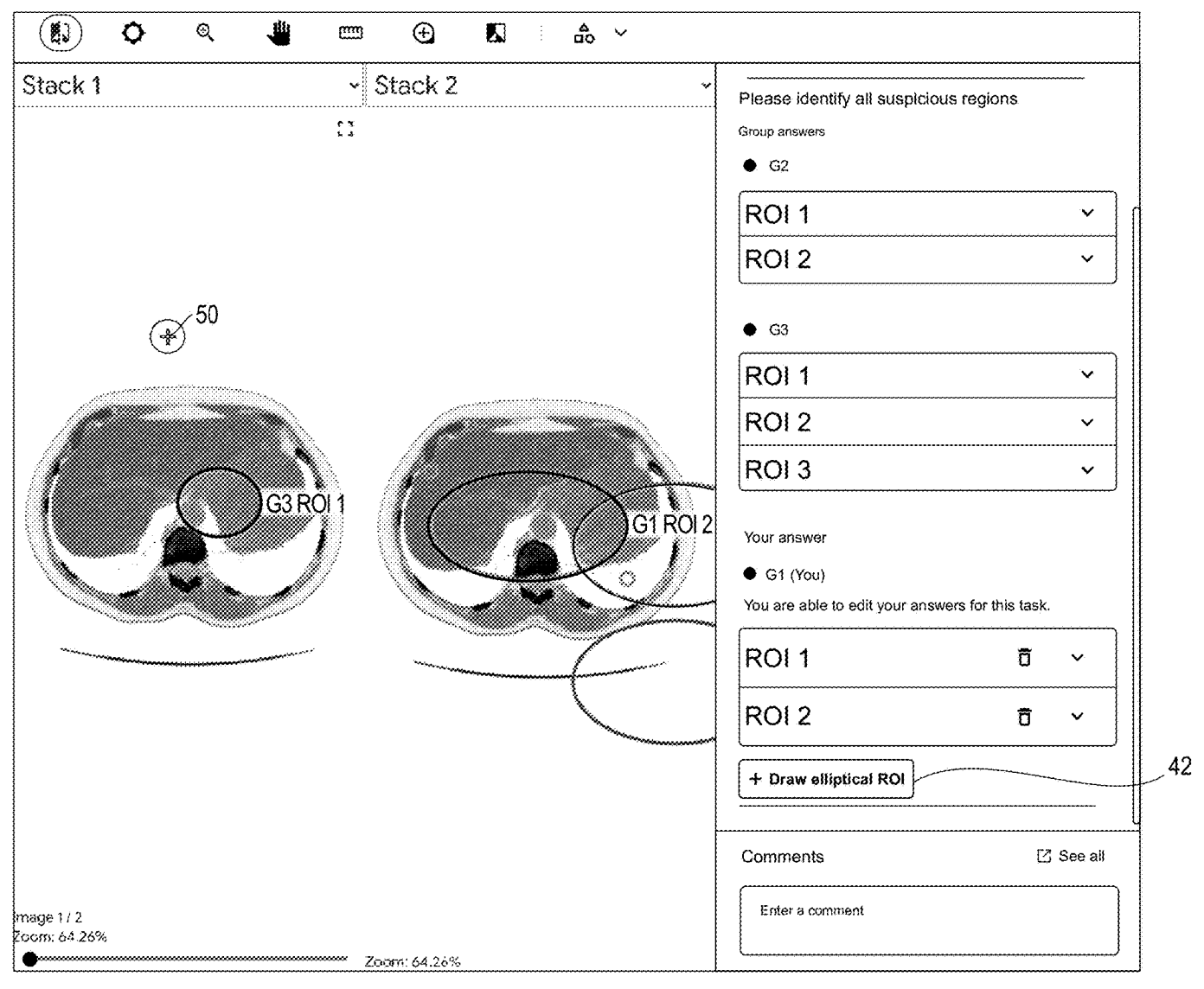

FIG. 8 is another example of the UI tool allowing the grader to assess the medical image and manually delineate one or more specific regions-of-interest (ROI) in the medical image. In this example they activate the "+draw elliptical ROI" icon 42 on the text panel on the right, they click on the image in "stack 1" and the small crosshair tool 50 appears in stack 1.

Figure 9:
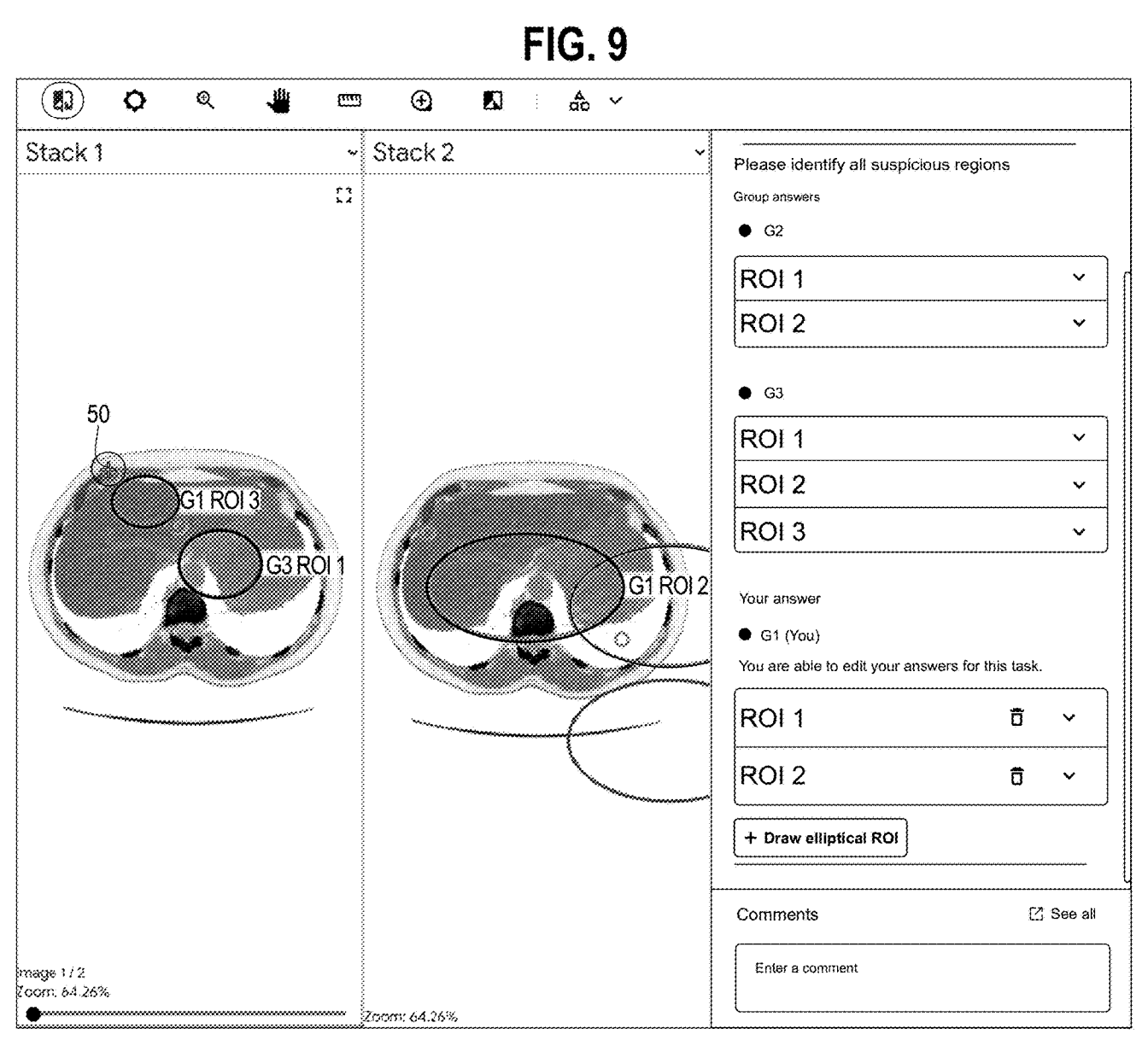

FIG. 9 shows the grader having dragged the crosshair tool 50 in stack 1 over to the image and releasing the crosshair tool 50 on the center of the area where the grader wishes to create an ellipse around the ROI. Handles (not shown, but see FIG. 3) on the crosshair tool permit the user to stretch the circle into the shape of an ellipse centered on the ROI.

The process shown in FIGS. 8 and 9 can be repeated to draw 2, 3 or more ROIs in any given medical image.

Figure 10:
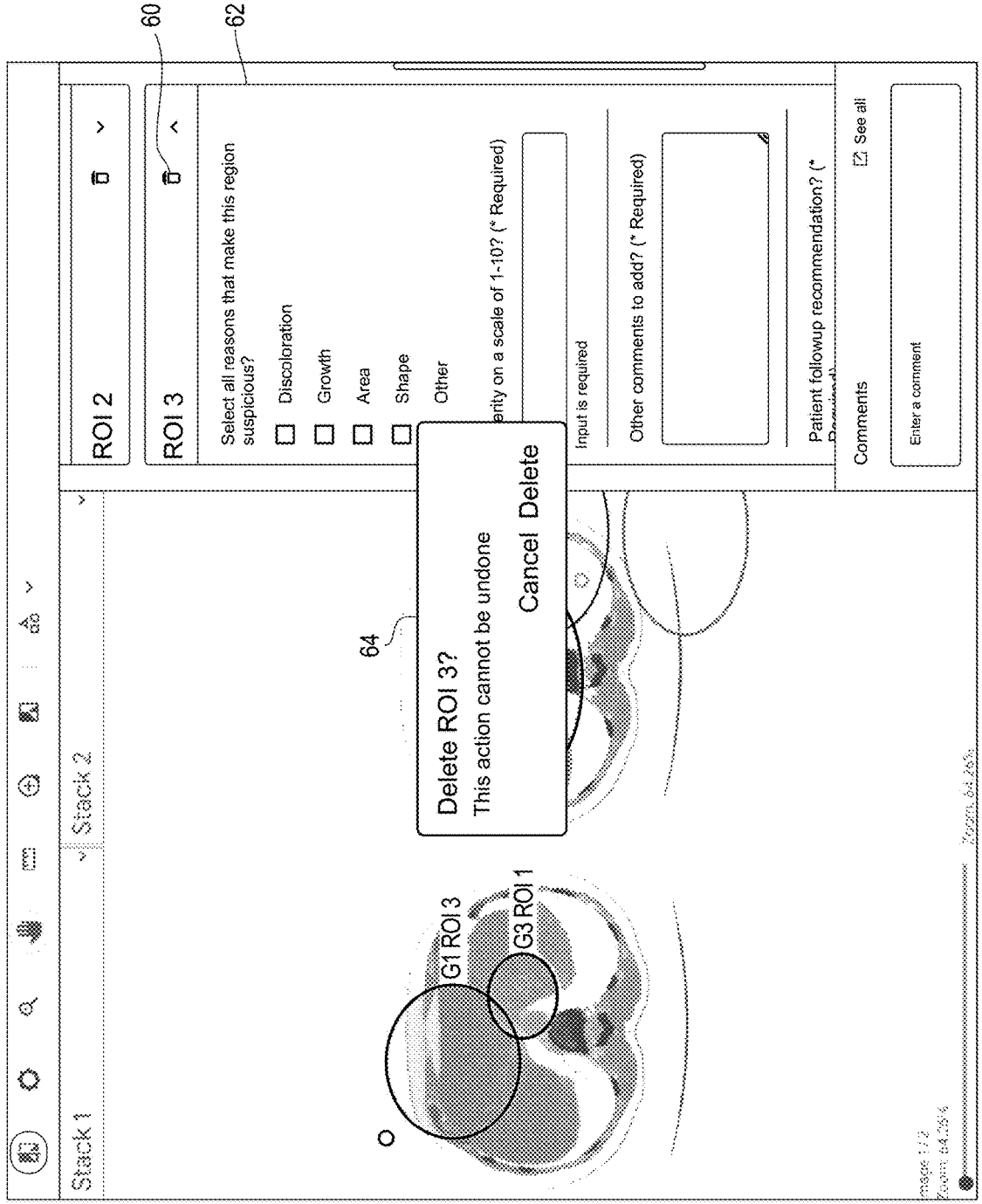
FIG. 10 is an illustration of the UI tool allowing the grader to delete an ROI.

FIG. 10 is an illustration of the UI tool allowing the grader to delete an ROI. If the grader wants to delete the ROI, they may click the trash icon 60 in the panel 62 for a particular ROI, in this example ROI 3. A confirmation dialog 64 will appear before it is deleted to ensure that the grader does not delete ROIs accidentally. The grader in ROI adjudication may only delete their own ROIs, not those of other graders.

Figure 11:
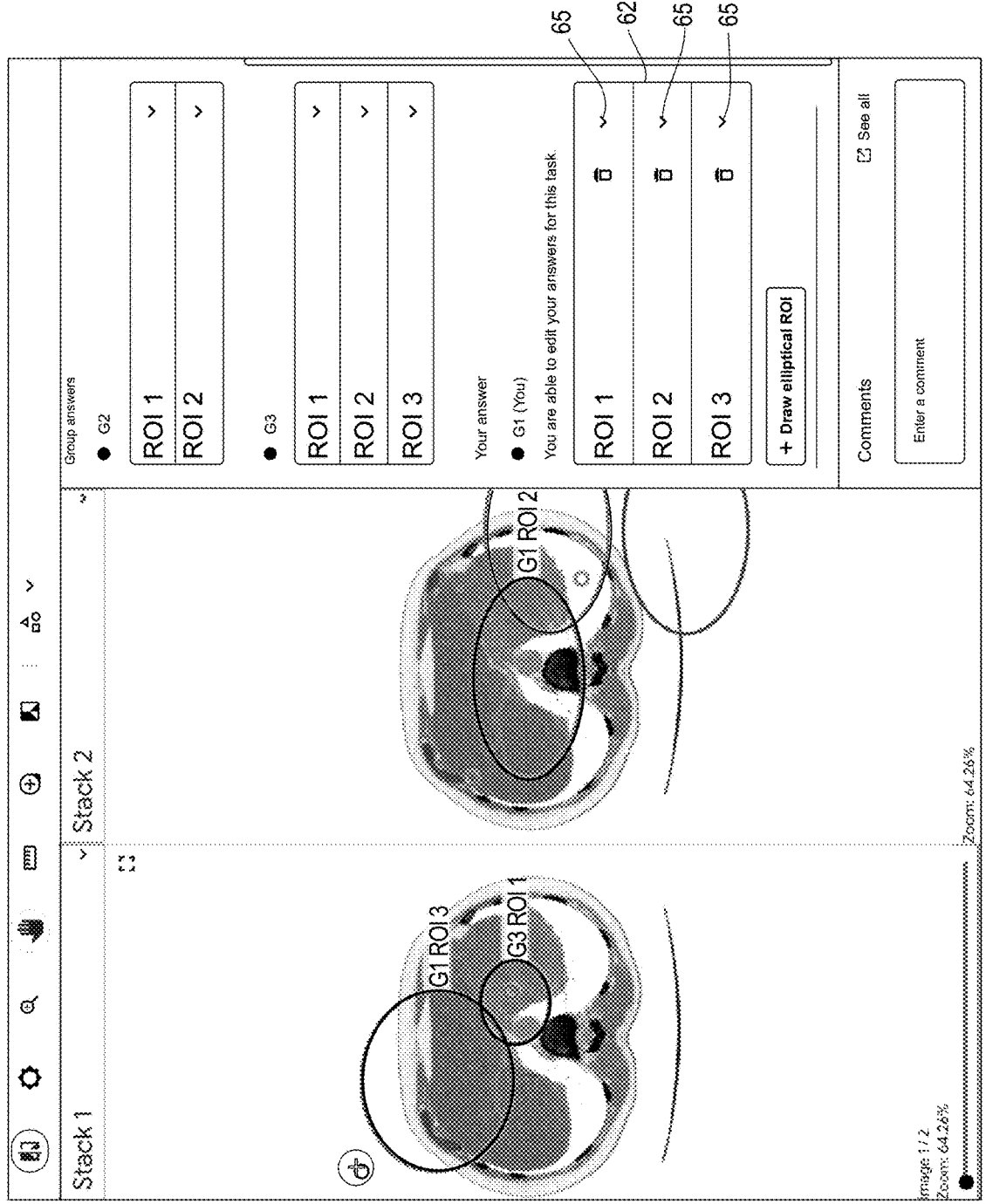
FIG. 11 is an illustration of a UI tool allowing a grader to edit an ROI or any comments or annotations they made about a selected ROI.

FIG. 11 is an illustration of a UI tool allowing a grader to edit an ROI or any comments or annotations they made about a selected ROI. If the grader wants to change the ROI, they may click on the ROI in the viewer or the associated prompt in the panel 62 and then drag one of the ROI handles to the new desired shape. The grader is also able to change any previously entered comments or annotations in the panel 62, accessible via the drop down tools 65.

(2) A Feature for Assessing the ROI Delineated by Other Graders, Including Display of the ROI Delineated by Other Graders.

FIG. 5 is an illustration of a UI tool in the form of a feature for assessing the ROI(s) delineated by other graders, including display of the ROI(s) delineated by other graders. In particular the Image Viewer includes a display of the ROI delineated by other graders superimposed on the medical images 12A and 12B. Each ROI is also identified in an anonymous manner with the grader that drew the ROI, and the number of the ROI, such as G3 ROI 1 (70) in image 12A. In this example grader G1 delineated ROI 2 (72) in image 12B. The panel 56 allows the grader to select any of the ROIs delineated by the other graders and read the comments and/or annotations they entered regarding the ROI, as shown at 74. The ROIs of the different graders are preferably displayed in contrasting colors in a consistent manner so as the help the grader identify which ROIs were drawn by which graders and avoid confusion with their own ROI(s).

(3) Dialog Features for Explaining and Discussing the Assessments,

The UI includes dialog features for explaining and discussion the assessments by the graders. These include a text feature permitting a grader to ask questions about a ROI delineated by other graders and permitting a grader to answer questions about the ROI they delineated. These dialog features and the ROIs delineated by all the graders are visible to all the graders on the workstation display as they adjudicate the medical image in a round-robin manner.

Preferably, the ROIs generated by the graders and any comments in the dialog features are associated with each grader in an anonymized format. That is, instead of identifying who the graders are by name, the ROIs and associated comments are associated with the grader in a completely anonymous manner such as by using the legend "G2", "G3" etc.

An example of this feature is shown in FIG. 6. The panel 56 includes a comment field 58 for entering questions and replies, and a check box 80, which when checked causes all the comments entered in the comment field to be displayed in a new panel 82. The panel 82 displays essentially a back and forth dialog between the graders. Such a dialog can include questions posed by a grader to another grader (or all other graders), and a response to a question from a grader. In this example, graders G1, G2 and G3 can proceed to ask questions, receive answers, and generally discuss their ROIs in a round-robin manner to ideally arrive at a consensus or agreement on the assessment of the medical image. In the example of FIG. 6, these back and forth questions, answers and comments are associated with ROI 1 designated by grader G3, but of course the display of the back and forth questions, answers and comments can be done for any of the ROIs of any of the graders by the grader selecting a particular ROI of a particular grader in the panel 56 and checking the check box ("see all") for reviewing all the comments regarding that particular ROI.

(4) A Feature for Manually Verifying Grader Agreement

Figure 7:
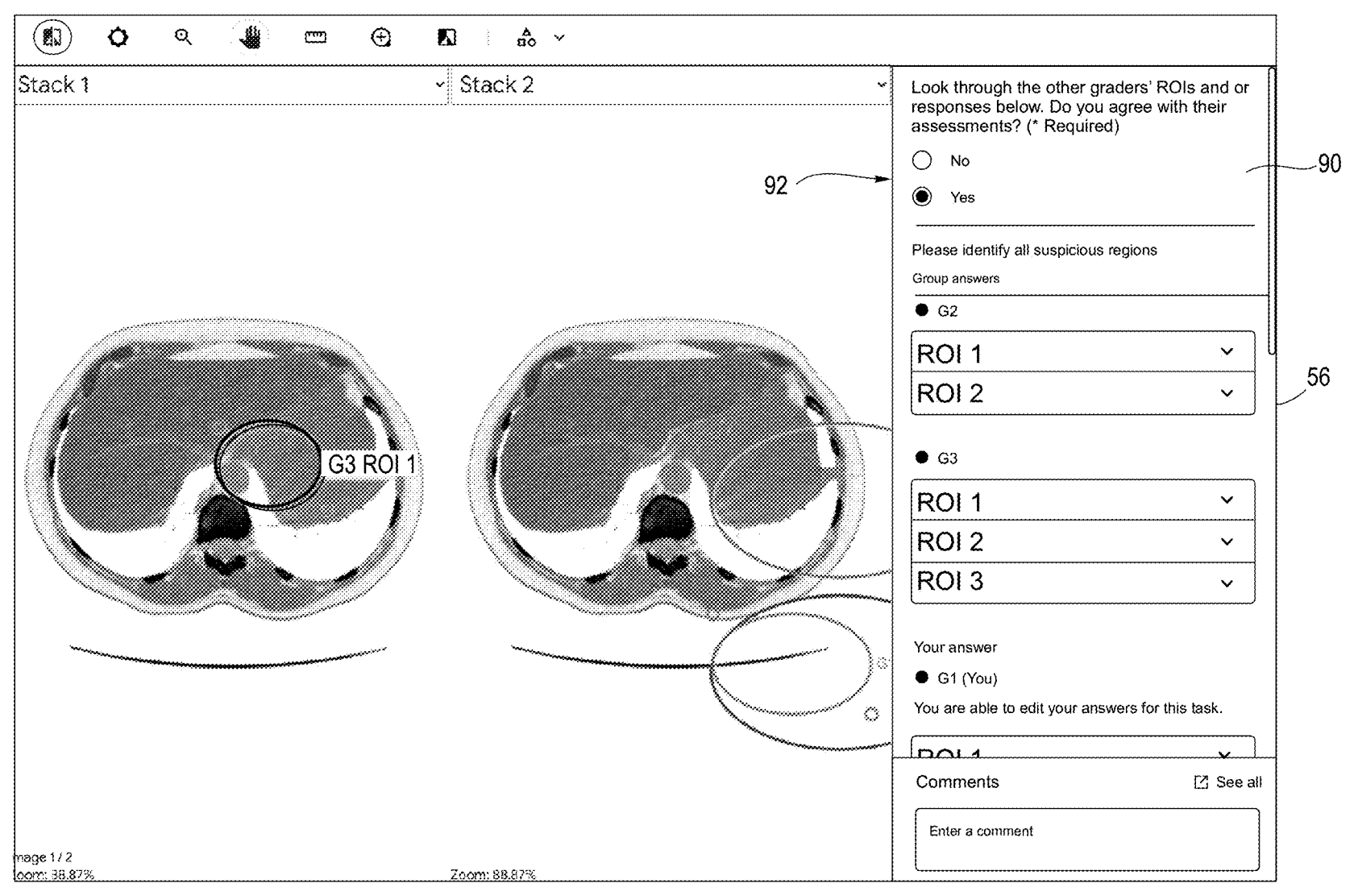

FIG. 7 is an illustration of a UI feature for manually verifying grader agreement. In this example, the panel 56 includes a dialog box 90 ("Look through the other graders' ROIs and/or responses below. Do you agree with their assessments?") and Yes and No buttons 92, activation of one of which is required. If each of the graders verify grader agreement by activating the Yes button the adjudication of the medical image is concluded. If one of the graders indicates agreement is not present by activating the No button, then the round-robin evaluation continues.

It is envisioned that in most cases adjudication will end with agreement among the graders after several rounds of adjudication. However, that will not always be the case. The administrator (or equivalent) may place a limit on the number of times in which the evaluation goes around to all the graders, or a limit on the amount of elapsed time since adjudication process started. If either of these limits are reached without unanimity in the assessment of the graders then adjudication ends, the case is flagged or marked as "no agreement", "indeterminate" or the equivalent, and the ROI's and all the comments are stored in the centrally stored digital file (FIG. 1, 22).

Image Viewer Layout

In the Image Viewer, the developer or administrator can configure different groupings of images for the grader to reference and annotate in a task. First, the grader (or organization using the Image Viewer) specifies the "layout" of the viewer, or how many "viewports" for images. The term "viewport" is used to refer to a slot or region where medical images will appear in the viewer. This can be 1×1 (1 viewport), 1×2 (2 viewports) see FIG. 12 as an example, 2×2 (4 viewports) see FIG. 13 as an example, or 2×4 (8 viewports). In each viewport, the developer can place one or more "stacks" of images. Each "stack" could contain one or more images, what we call "slices." The grader is then able to navigate among the slices and stacks in each viewport in the viewer for their task, and for each slice, delineate ROI, provide comments and annotations, review ROI(s) and comments from other graders, etc.

Figure 12:
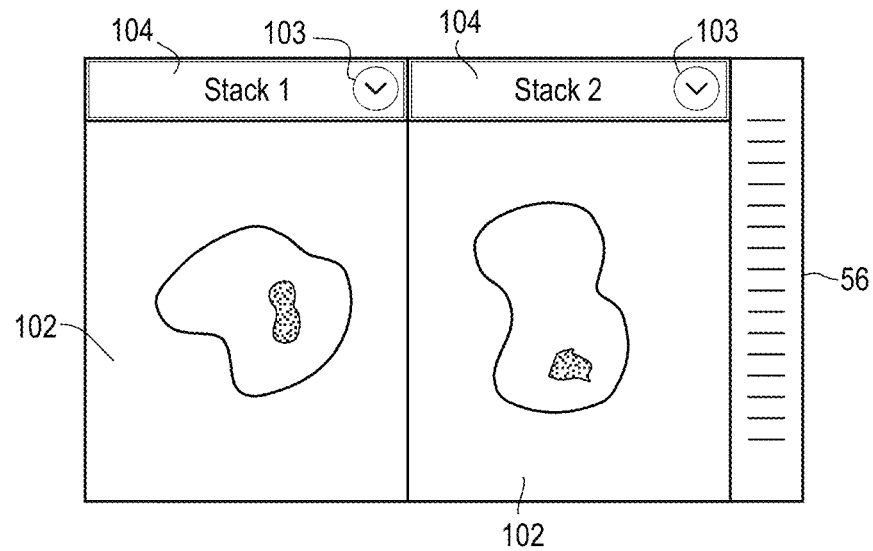
FIG. 12 is an illustration of the workstation display showing what is referred to as a 1×2 viewport.

FIG. 12 is an illustration of the workstation display showing what is referred to as a 1×2 viewport, each viewport 102 consisting of a stack of images identified as "stack 1", "stack 2". Within each stack are multiple "slices" which could for example be different planes of a 3D image. The user navigates between the different viewports and slices using the dropdown tools 103 in the top toolbar 104. For any given slice that is displayed the tools in the side panel 56 allow for the user to review the image, delineate ROI, comment on ROI, and indicate whether agreement exists with other graders' assessments, as described previously.

Figure 13:
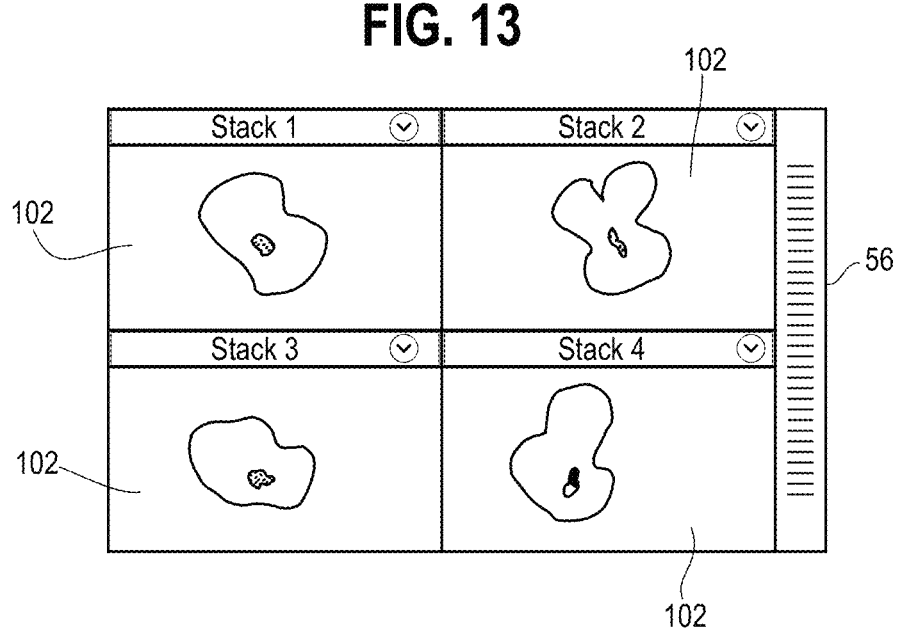
FIG. 13 in illustration of the workstation display configured as a 2×2 viewport. The display may be configured in many different possible viewports (e.g., 1×3, 2×3, 1×4, etc.), depending on grader preferences, the type of images being reviewed, the number or type of imaging modalities or views for a given patient and other factors, the details of which are not particularly important.

FIG. 13 in illustration of the workstation display configured as a 2×2 viewport with four viewports 102. The display may be configured in many different possible viewports (e.g., 1×3, 2×3, 1×4, etc.), depending on grader preferences the type of images being reviewed, the number or type of imaging modalities or views for a given patient and other factors, the details of which are not particularly important.

Very often, the graders will have an entire grading task represent one patient. That would mean that each viewport 102 has one or more images of a different type of the same patient. Consider the following example of mammography. Commonly, one patient's mammogram will produce 4 images: Left CC, Right CC, Left MLO, Right MLO. The labeling task may require a grader to look at 5 years of one patient's mammogram images and track the growth of a tumor over that time. Let's say the prompts present in the panel 56 ask the grader to "Find and circle the first instance of any and all tumors" and then answer questions about the tumors. In that case, the developer or administrator might arrange the viewer to display 2×2 viewports as shown in FIG. 13. The developer or administrator may choose to have each viewport contain all 5 years of images of the same image type, Left CC for instance. The developer or administrator would then choose to have a Stack of Left CC images in Viewport 1, which contains 5 slices, each slice being a Left CC for a specific year. That would then be Stack 1 containing these slices: 2020 L CC, 2019 L CC, 2018 L CC, 2017 L CC, 2016 L CC. The reason for this is so that a grader could look through the same view over 5 years to compare. Furthermore, by means of the dropdown tool 103, the grader can choose the year 2019 for all the viewports to see the full slate of all four mammogram images obtained in 2019 displayed in all four viewports 102 at the same time in the same display.

It will be appreciated that the developer or administrator may use the different components in other ways too. Our tooling does not restrict or recommend any content in particular. That is simply one example for Mammography, which is a type of medical image these complex layouts were optimized for.

3D Volume Images

The medical images being graded in this disclosure could take the form of 3D image composed of multiple slices (images) obtained in different planes. Examples of this are a set of Z-stack magnified images of a tissue specimens, and a CT scan taken through different planes of an organ or body part. In one possible configuration, the set of user interface features (1)-(4) described above permit delineation of ROIs and the discussion of the ROIs between the graders, including entry of text questions and answers, in each of the slices. In one possible configuration, the tool for manually verifying grader agreement prompts the graders to verify grader agreement for the medical image as a whole.

Further Considerations and Use Cases

While one aspect of the this disclosure is the UI features described above and illustrated in the figures, one additional aspect of this disclosure is that the UI tools and round-robin adjudication method can produce a set of one or more medical images that is associated with the adjudication, including the delineated ROI(s) and associated comments and discussions. For example, a digital file is created that includes data representing (a) the set of one or more medical images, (b) the associated delineated ROI(s) and (c) text in the form of comments from the graders on the ROIs. When the process is conducted on a large number of medical images a large number of digital files as described are created. These files can then be used as labeled training examples for a machine learning model, e.g., being trained to identify areas of interest, generate a diagnosis, or other medical task. The set of digital files can also be used in an exercise of validating a machine-learning model, e.g., assessing its performance or generating statistics of model performance.

As another possible use case, the round-robin asynchronous grading using the tools of FIGS. 1 and 2 could be used in a clinical diagnosis scenario, where the graders G1, G2 . . . represent different physicians which review medical images for a given patient, delineate ROI(s) in the image, create comments and discussion about the ROI(s) in the text features, and then indicate (typically) mutual agreement in the assessment. The resulting medical image with the ROI(s) and comments can then be provided to the patient's primary care physician, a specialist treating the patient, or directly to the patient.

One possible variation in this use case is that a machine learning model can be trained from the labelled examples provided by this methodology, and one of the "graders" is the trained machine learning model, in which the model itself created one or more ROIs in the medical image. The commentary of the other graders reviewing the medical image will include commentary on the machine learning model ROI(s).

Thus in one further aspect we envision a distributed clinical diagnostic computer system in the form of one or more workstations (see FIG. 1) including set of tools as described above.

From the foregoing description, it will be appreciated that we have described a method of performing an asynchronous adjudication of one or more regions-of-interest in a medical image by a group of two or more graders, each of which has access to the set of tools at a workstation in which the workstation includes a display displaying the medical image, comprising the steps of (1) providing each of the graders with user interface feature enabling the grader to assess the medical image and manually delineate one or more specific regions-of-interest (ROI) in the medical image on the workstation display (FIGS. 2, 3, 4, 8, 9);

(2) providing each of the graders with a user interface feature for assessing the ROI delineated by other graders, including display of the ROI delineated by other graders (FIGS. 5, 8, 11)

(3) providing each of the graders with dialog features for explaining and discussing the assessments, including a text feature permitting a grader to ask questions about a ROI delineated by other graders and permitting a grader to answer questions about the ROI they delineated wherein the dialog features and the ROIs delineated by all the graders are visible to all the graders on their respective workstation display as they adjudicate the medical image in a round-robin, asynchronous manner (FIG. 6); and (4) providing each of the graders with a user interface feature for manually verifying grader agreement (FIG. 7), wherein if each of the graders verify grader agreement using the feature the adjudication of the medical image is concluded.

It will also be apparent that the server environment (server 11 and memory 13) of FIG. 1 can be considered as a computing platform facilitating asynchronous adjudication of one or more regions-of-interest in a medical image by a group of two or more remotely located graders. The graders communicate with the computing platform (11, 13) over computer networks (20) using workstations as shown in FIG. 1. The computing platform includes the computer memory (e.g., mass data storage unit) 13 storing the medical image, and a server 11 distributing the medical image to the workstations (16) used by the two or more graders. The server 11 receives data from the workstations indicating the graders' assessment of the medical image and manually delineation of one or more specific regions-of-interest (ROI) in the medical image as explained previously. The server 11 further receives data from the workstations in the form of text by which the graders assess the ROI delineated by other graders. The server further receives data from the workstations in the form of text explaining and discussing the assessments, optionally including questions about a ROI delineated by other graders and answer to questions about the ROI they delineated, examples of which are shown in the Figures. The server 11 communicates with the workstations such that the text and ROIs delineated by all the graders are visible to all the graders on the workstation display as they adjudicate the medical image in a round-robin manner. The server further receives data indicating manually verifying grader agreement, indicating that the adjudication of the medical image is concluded.

In view of the above, it will also be appreciated that a method of performing an asynchronous adjudication of one or more regions-of-interest in a medical image by a group of two or more graders has been disclosed. Each of the graders has access to the set of tools at a workstation in which the workstation includes a display displaying the medical image, see FIG. 1. The method includes the steps of (1) receiving and storing in an adjudication computing platform (server 11 and memory 13) data manually delineating one or more specific regions-of-interest (ROI) in the medical image from the workstations; (2) receiving and storing in the adjudication computing platform data comprising text from the workstations explaining and discussing the assessments, including a text asking questions about a ROI delineated by other graders and answers to questions about the ROI a grader delineated, wherein adjudication computing platform communicates with the workstations such that the text and the ROIs delineated by all the graders are visible to all the graders on their respective workstations as they adjudicate the medical image in a round-robin, asynchronous manner; and (3) receiving and storing data indicating manual agreement from each of the graders on the adjudication of the ROIs.

In one embodiment, a computer-readable medium (e.g., memory, e.g., memory 13) stores non-transient software instructions which perform the method as recited herein.

The appended claims are offered as further descriptions of the disclosed subject matter.

We claim:

1. A method of performing an asynchronous adjudication of one or more regions-of-interest in a medical image by a group of two or more graders, each of which has access to a set of tools at a workstation in which the workstation includes a display displaying the medical image, comprising:
    providing each of the graders with a first user interface feature enabling the grader to assess the medical image and manually delineate one or more specific regions-of-interest (ROI) in the medical image on the workstation display;
    providing each of the graders with a second user interface feature for assessing the ROI delineated by other graders, including display of the ROI delineated by other graders;
    providing each of the graders with dialog features for explaining and discussing the assessments, including a text feature permitting a grader to ask questions about a ROI delineated by other graders and permitting a grader to answer questions about the ROI they delineated wherein the dialog features and the ROIs delineated by all the graders are visible to all the graders on their respective workstation display as they adjudicate the medical image in a round-robin, asynchronous manner;
    providing each of the graders with a third user interface feature for manually verifying grader agreement; and
    responsive to receiving indications of grader agreement from all of the graders via respective third user interface features, concluding the adjudication of the medical image.

2. The method of claim 1, further comprising, subsequent to providing the first user interface features to a first grader of the group of two or more graders:
    receiving, from the first grader via the first user interface feature, a manual delineation of a first specific ROI; and
    subsequently receiving, from a second grader of the group of two or more graders, a request to perform asynchronous adjudication of the one or more ROIs of a medical image, wherein providing each of the graders with the first user interface feature and the second user interface feature comprises, responsive to receiving the request from the second grader, providing the second grader with the first user interface feature and the second user interface feature that includes display of the first specific region-of-interest delineated by the first grader.

3. The method of claim 2, further comprising:
receiving, from the second grader via the first user interface feature, a manually-delineation of a second specific ROI; and
subsequently receiving, from a third grader of the group of two or more graders, a request to perform asynchronous adjudication of the one or more ROIs of a medical image, wherein providing each of the graders with the first user interface feature and the second user interface feature comprises, responsive to receiving the request from the third grader, providing the third grader with the first user interface feature and the second user interface feature that includes display of the first and second specific ROIs.

4. The method of claim 1, further comprising permitting each of the graders to generate, using the first user interface feature, a ROI in the medical image in the form of a closed curve, a point, a line, and/or a line segment.

5. The method of claim 1, wherein the ROIs delineated by each user using the first user interface feature and any comments provided by each user using the dialog features are associated with each grader in an anonymized format.

6. The method of claim 1, further comprising, subsequent to providing the first user interface features to a first grader of the group of two or more graders:
receiving, from a first grader of the two or more graders via the first user interface feature, a manual delineation of a first specific ROI;
subsequently providing, to a second grader of the two or more graders via the second user interface feature, a display of the first specific ROI;
subsequently receiving, from the second grader via the text feature, a first question about the first specific ROI;
responsively providing, to the first grader via the text feature, a display of the first question;
subsequently receiving, from the first grader via the text feature, a first answer; and
responsively providing, to the second grader via the text feature, a display of the first answer.

7. The method of claim 6, wherein the tool for manually verifying grader agreement prompts the graders to verify grader agreement for the medical image as a whole.

8. The method of claim 6, further comprising, based on ROIs generated by graders interacting with the user interface feature(s) and based on medical images related thereto, training an ML model to automatically generate an ROI for an input medical image.

9. A computing platform providing asynchronous adjudication of one or more regions-of-interest in a medical image by a group of two or more remotely located graders in communication with the computing platform over a computer network using a workstation, comprising:
a computer memory storing the medical image; and
a server distributing the medical image to the workstations used by the two or more graders, wherein the server receives data from the workstations indicating the graders' assessment of the medical image and manual delineation of one or more specific regions-of-interest (ROI) in the medical image;
wherein the server further receives data from the workstations in the form of text by which the graders assess the ROI delineated by other graders;
wherein the server further receives data from the workstations in the form of text explaining and discussing the assessments, optionally including questions about a ROI delineated by other graders and answer to questions about the ROI they delineated; wherein the server communicates with the workstations such that the said text and ROIs delineated by all the graders are visible to all the graders on the workstation display as they adjudicate the medical image in a round-robin manner;
wherein the server further receives data indicating manual verification of grader agreement and
wherein the server, responsive to receiving data indicating manual verification of grader agreement from all of the graders, concludes adjudication of the medical image.

10. The computing platform of claim 9, wherein the server further receives, from a first grader of the group of two or more remotely located graders subsequent to receiving, from a second grader of the group of two or more remotely located graders, data indicating the second grader's delineation of a first specific ROI, a request to perform asynchronous adjudication of the one or more ROIs of a medical image, and
wherein the server communicating with the workstations such that the said text and ROIs delineated by all the graders are visible to all the graders on the workstation display as they adjudicate the medical image in a round-robin manner comprises the server, responsive to receiving the request from the first grader, communicating with a workstation of the first grader to provide a display of the first specific ROI to the first grader.

11. The computing platform of claim 9, wherein the manually delineated ROI is in the form of a closed curve, a point, a line, and/or or a line segment.

12. The computing platform of claim 9, wherein said text and ROIs manually delineated by the graders are presented on the workstations in an anonymized format.

13. The computing platform of claim 9, wherein the server additionally:
communicates with a workstation of a first grader of the group of two or more remotely located graders to provide, to the first grader, a display of a first specific ROI delineated by a second grader of the group of two or more remotely located graders;
receives, from the workstation of the first grader, a first question about the first specific ROI;
responsive to receiving the first question, communicates with a workstation of the second grader to provide, to the second grader, a display of the first question;
receives, from the workstation of the second grader, a first answer; and
responsive to receiving the first answer, communicates with the workstation of the first grader to provide, to the first grader, a display of the first.

14. The computing platform of claim 9, wherein the server additionally trains, based on the medical image and the data from the workstations indicating the graders' assessment of the medical image and manually delineation of one or more specific regions-of-interest (ROI) in the medical image, an ML model to automatically generate an ROI for an input medical image.

15. A non-transitory computer-readable medium, having stored thereon program instruction that, upon execution by a computing device, cause the computing device to perform a method of performing an asynchronous adjudication of one or more regions-of-interest in a medical image by a group of two or more graders, each of which has access to a set of tools at a workstation in which the workstation includes a display displaying the medical image, comprising:
providing each of the graders with a first user interface feature enabling the grader to assess the medical image and manually delineate one or more specific regions-of-interest (ROI) in the medical image on the workstation display;

providing each of the graders with a second user interface feature for assessing the ROI delineated by other graders, including display of the ROI delineated by other graders;

providing each of the graders with dialog features for explaining and discussing the assessments, including a text feature permitting a grader to ask questions about a ROI delineated by other graders and permitting a grader to answer questions about the ROI they delineated wherein the dialog features and the ROIs delineated by all the graders are visible to all the graders on their respective workstation display as they adjudicate the medical image in a round-robin, asynchronous manner;

providing each of the graders with a third user interface feature for manually verifying grader agreement; and responsive to receiving indications of grader agreement from all of the graders via respective third user interface features, concluding the adjudication of the medical image.

16. The non-transitory computer-readable medium of claim 15, wherein the method further comprises, subsequent to providing the first user interface features to a first grader of the group of two or more graders:

receiving, from the first grader via the first user interface feature, a manual delineation of a first specific ROI; and subsequently receiving, from a second grader of the group of two or more graders, a request to perform asynchronous adjudication of the one or more ROIs of a medical image, wherein providing each of the graders with the first user interface feature and the second user interface feature comprises, responsive to receiving the request from the second grader, providing the second grader with the first user interface feature and the second user interface feature that includes display of the first specific region-of-interest delineated by the first grader.

17. The non-transitory computer-readable medium of claim 16, wherein the method further comprises:

receiving, from the second grader via the first user interface feature, a manually-delineation of a second specific ROI; and subsequently receiving, from a third grader of the group of two or more graders, a request to perform asynchronous adjudication of the one or more ROIs of a medical image, wherein providing each of the graders with the first user interface feature and the second user interface feature comprises, responsive to receiving the request from the third grader, providing the third grader with the first user interface feature and the second user interface feature that includes display of the first and second specific ROIs.

18. The non-transitory computer-readable medium of claim 15, wherein the method further comprises, subsequent to providing the first user interface features to a first grader of the group of two or more graders:

receiving, from a first grader of the two or more graders via the first user interface feature, a manual delineation of a first specific ROI;

subsequently providing, to a second grader of the two or more graders via the second user interface feature, a display of the first specific ROI;

subsequently receiving, from the second grader via the text feature, a first question about the first specific ROI;

responsively providing, to the first grader via the text feature, a display of the first question;

subsequently receiving, from the first grader via the text feature, a first answer; and responsively providing, to the second grader via the text feature, a display of the first answer.

19. The non-transitory computer-readable medium of claim 15, wherein the method further comprises-permitting each of the graders to generate, using the first user interface feature, a ROI in the medical image in the form of a closed curve, a point, a line, and/or a line segment.

20. The non-transitory computer-readable medium of claim 15, wherein the ROIs delineated by each user using the first user interface feature and any comments provided by each user using the dialog features are associated with each grader in an anonymized format.

* * * * *